United States Patent [19]

Herman

[11] Patent Number: 5,171,296
[45] Date of Patent: Dec. 15, 1992

[54] STEREOTAXIC HEADRING FIXATION SYSTEM AND METHOD

[75] Inventor: Martin D. Herman, Chicago, Ill.

[73] Assignee: Northwestern University, Evanston, Ill.

[21] Appl. No.: 739,919

[22] Filed: Aug. 2, 1991

[51] Int. Cl.⁵ ............................ A61F 5/00; A61B 19/00
[52] U.S. Cl. .......................................... 602/5; 602/17; 602/18; 602/19; 606/130
[58] Field of Search ........... 606/130; 128/76 R, 87 B, 128/75, 84 C, 78, 69; 602/17, 18, 19, 32, 5

[56] References Cited

U.S. PATENT DOCUMENTS

| | | | |
|---|---|---|---|
| 678,417 | 7/1901 | Muller | 128/87 B |
| 2,091,759 | 8/1937 | Johnson | 128/87 B |
| 2,223,276 | 11/1940 | Ward | 128/87 B |
| 3,724,452 | 4/1973 | Nitschke | 602/18 |
| 3,795,243 | 3/1974 | Miller | 128/87 B |
| 3,957,040 | 5/1976 | Calabrese | 128/87 B |
| 4,541,421 | 9/1985 | Iversen | 128/87 B |
| 4,620,530 | 11/1986 | Lanier | 128/87 B |
| 4,628,913 | 12/1986 | Lerman | 128/78 |
| 4,643,099 | 12/1986 | Mollo | 128/87 B |
| 4,793,334 | 12/1988 | McGuinness | 128/87 B |
| 4,807,605 | 2/1989 | Mattingly | 128/78 |
| 5,010,881 | 4/1991 | Boudreau | 128/87 B |

Primary Examiner—Michael A. Brown
Attorney, Agent, or Firm—Tilton, Fallon, Lungmus

[57] ABSTRACT

A system for applying a stereotaxic headring, as used in neurosurgery, in which a brace performs the functions of immobilizing a patient's head with respect to the shoulders and upper torso and also of rigidity supporting the headring in a selected position of adjustment. The brace therefore fixes both the head and headring against relative movement, allowing the headring to be anchored directly to the patient's skull in the precise position selected. Once the headring is so anchored, the brace may be removed and conventional stereotaxic neurosurgical procedures may be undertaken.

9 Claims, 2 Drawing Sheets

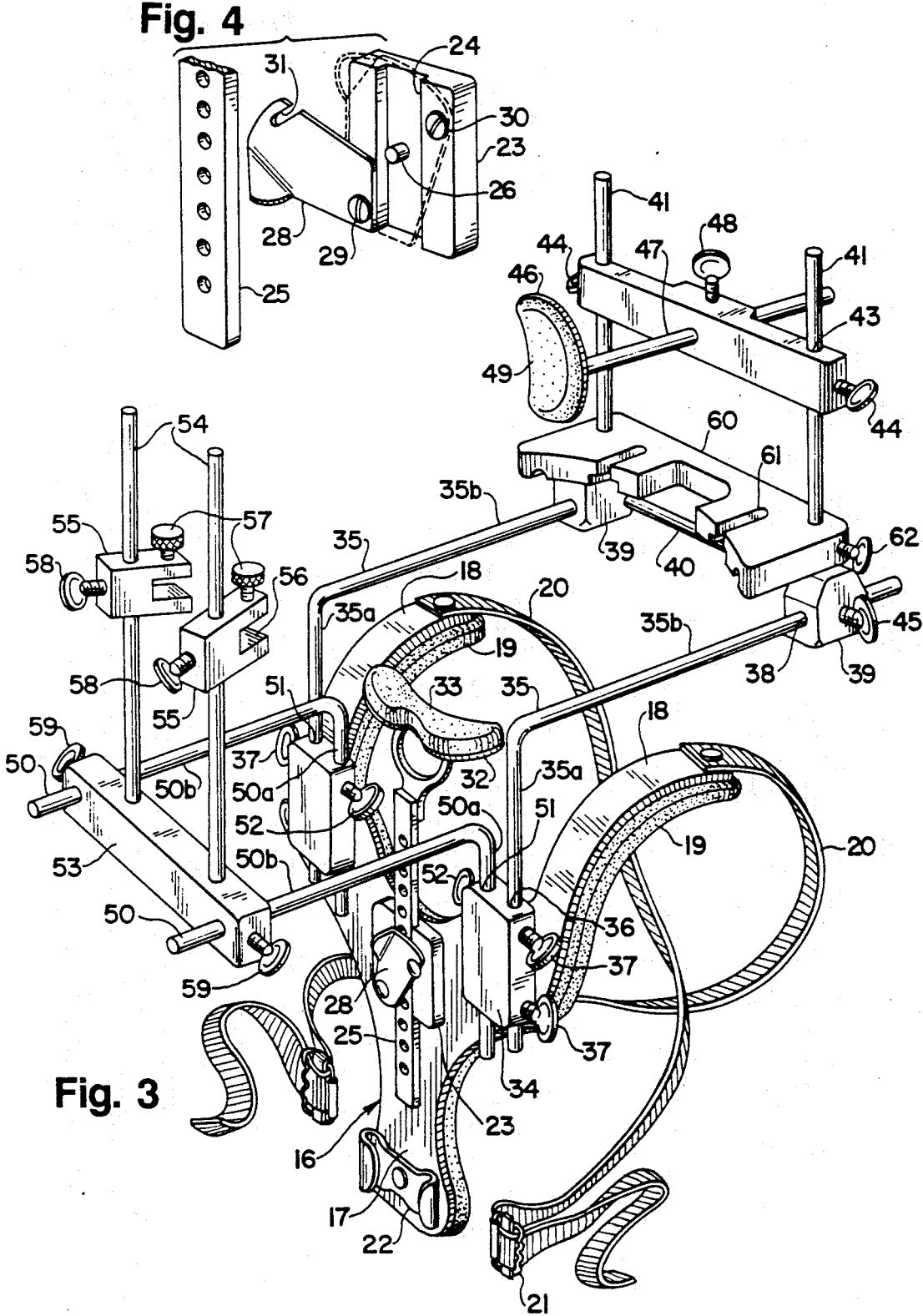

STEREOTAXIC HEADRING FIXATION SYSTEM AND METHOD

BACKGROUND AND SUMMARY

In stereotaxic neurosurgery, a headring is secured to a patient's skull, a localizing unit is affixed to the headring, and then, utilizing medical imaging modalities such as computed tomography (CT), magnetic resonance imaging (MRI), digital substraction venous angiography (DSVA) or positron emission tomographical scanning (PET), a target point for the lesion in the brain is established. The headring, which is immobilized in relation to the patient's head, thereafter serves as the base for attaching what is known as an arc system, and it is in relation to the arc system that the possible entry points, angular settings, and distances to the target point are computed. Following selection of the entry point, an appropriate instrument, such as a biopsy instrument, is supported by the arc system for carrying out the selected medical procedure.

Therefore, a key to all such procedures is fixing the headring in a selected position to the upper portion of a patient's skull (calvarium). In the past, that has usually been carried out while a patient is under general anesthetic even though there could be substantial advantages in performing such a step while the patient is awake. (Brain tissue has no nerve sensors and local anesthetics would eliminate pain associated with forming the small surgical entry opening or attaching the headring to the patient's skull.) If no general anesthetics were required, the risks and costs of such an operation would be reduced, no hospitalization would be necessary and the entire procedure, which generally takes less than one hour, might be performed on an outpatient basis. However, a main problem with performing such a procedure while a patient is awake is that patients requiring neurosurgery may be, partly by reason of their affliction, uncooperative, confused, or obtunded. Discomfort, or fear of discomfort, may also be involved. Such factors may result in head movements that could make it difficult, if not impossible, for a surgical team to anchor a stereotaxic headring in a precise position on a patient's head while the patient remains awake.

Prior efforts to stabilize a headring have involved the use of Velcro-type straps (as in the Brown-Roberts-Wells (BRW) stereotaxic system) or bars inserted into the auditory meatus (as in the Leksell system), but neither arrangement insures against relative movement between a ring and patient's head or does anything to immobilize the head itself. Therefore, general anesthetics have still been considered necessary.

Accordingly, one aspect of this invention lies in recognizing that the aforementioned problems could be overcome, and a stereotaxic headring could be applied even while a patient is awake, if, first, a patient's head were immobilized or fixed against movement relative to the shoulders and upper torso, and second, a stereotaxic headring were then adjusted and fixed in relation to the same rigid brace used to immobilize the head. Since both the head and headring would be fixed in relation to the patient's shoulders and torso, they would be fixed in relation to each other.

Once a patient's head is so immobilized and a stereotaxic headring is supported by the brace in its selected position of adjustment, local anesthetics may be applied at the entry or attachment points and nylon screws may be used in the usual manner to secure the headring to the patient's calvarium. Thereafter, the brace may be removed, leaving the headring fixed to the patient's head for use as stereotaxic neurological procedures require.

Briefly, the bracing means for the stereotaxic headring takes the form of a rigid body plate, preferably in the form of a chest plate, having a pair of shoulder rests that extend over a patient's shoulders. Straps are secured to the shoulder rests and plate for immobilizing the plate with respect to a patient's shoulders and upper torso. A plurality of support members in the form of rigid bars are adjustably mounted on the body plate, and clamps are adjustably fixed to the support members for supporting a stereotaxic headring at circumferentially-spaced points. A chin support is adjustably secured to the body plate, and a rear head support is also adjustably anchored to the body plate for contacting the occipital area and posteriorly bracing the head. The head support and chin support, in combination with the body plate, immobilize the head in relation to the upper torso, and the support members and clamps anchor the stereotaxic headring against movement with respect to the brace and, hence, with respect to the patient's head.

Other features, advantages, and objects of the invention will become apparent from the specification and drawings.

DRAWINGS

FIG. 3 is an enlarged perspective view similar to FIG. 1 but omitting the stereotaxic headring.

FIG. 4 is a still further enlarged exploded perspective view illustrating the supporting mechanism for the chin support.

DETAILED DESCRIPTION OF PREFERRED EMBODIMENT

Figure 1:
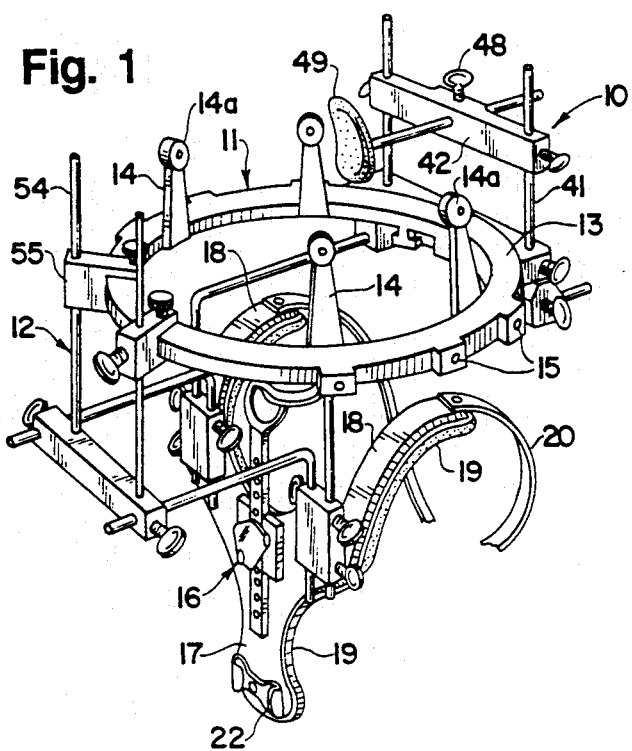
FIG. 1 is a perspective view of a stereotaxic headring supported by bracing means in accordance with this invention.

Referring to FIG. 1, the numeral 10 generally designates a combination of a stereotaxic headring or headframe 11 and bracing means 12 for fixing the head against movement with respect to the shoulders and upper torso and for supporting the headring in a selected position of adjustment. The headring as shown is of the general type utilized in the aforementioned BRW stereotaxic system, and includes a ring portion 13 and a plurality of upstanding fixation posts 14 secured to the ring portion and provided at their upper ends with apertures 14a for receiving fixation screws. Other apertures 15 are provided for attachment of the localizing unit and the arc guidance system (not shown) as used in the BRW system. It is to be understood, however, that while a stereotaxic ring of the type used in the BRW system is shown for purposes of illustration, other types of headrings as known in stereotaxic neurosurgery may be used.

The brace 12 includes a rigid body plate 16 of generally Y-shaped configuration, having a lower torso engaging portion 17 and a pair of upper shoulder rest portions 18. The lower and upper portions are integrally formed, with the shoulder rest portions being spaced apart and curving gradually upwardly and rearwardly to conform with the contour of a patient's shoulders. Ideally, lower portion 17 is shaped and dimensioned to bear against a patient's chest in the region of the sternum. Resilient cushioning 19 extends along the rear (posterior) surfaces of the body plate 16, and along shoulder portions 18, to promote a secure and comfortable fit of the plate against the chest and shoulders. Flexible straps 20 are connected to the shoulder portions 18 and are provided with adjustable buckles that may be clipped to the curved ends of an attachment bracket 22 mounted near the front end of the lower portion 17 of the body plate (FIG. 3). In use, the straps are preferably crossed over the patient's back and the buckles are adjusted so that the straps and body plate are in snug contact with the patient's chest when the buckles are attached to the bracket, thereby securing the rigid body plate 16 against movement in relation to the patient's shoulders and upper torso.

Body plate 16 serves as the mounting member for a plurality of elements that may be adjusted to brace a patient's head against movement with respect to the plate. Referring to FIGS. 3 and 4, a mounting block 23 is secured to the face of the body plate and is provided with a vertical channel 24 for receiving vertically-elongated bar 25. A pin 26 within the channel may be received in any of a series of openings 27 in the bar, and a locking cover 28 is pivotally connected to the mounting block by pivot 29. When the bar 25 is received in the channel in a selected position of adjustment, cover 28 may be swung into the closed position depicted in FIG. 3 (and in broken lines in FIG. 4) and, if desired, screw 30, which extends through a slot 31 in the cover, may be tightened to insure that the cover cannot become inadvertently opened during use.

At its upper end, bar 25 is equipped with a transversely-extending chin plate 32 that is provided with resilient cushioning 33 along its upper surface. The cushioned chin plate 32, upstanding bar 25, and mounting block 23 with its locking cover 28, operate together as chin supporting means for bracing a patient's head against forward, and to some extent lateral, movement.

Means are also provided for bracing the rear (posterior) or occipital portion of the patient's head. Such means takes the form of a pair of mounting blocks 34, secured to the face of body plate 16 on opposite sides of the central mounting block 23, and an arrangement of frame members and other elements that are connected to blocks 34, as shown most clearly in FIG. 3. A pair of L-shaped support members or bars 35 have vertical portions 35a slidably received in vertical openings 36 in the mounting blocks, and thumbscrews 37, threadedly received in intersecting openings, may be tightened to secure the bars in selected positions of adjustment. The bars also include horizontal portions 35b which extend rearwardly (posteriorly) over the patient's shoulders and are received in openings 38 in a pair of connecting blocks 39, such blocks being joined by a transverse horizontal bar 40. Vertical bars 41 are fixed at their lower ends to connecting blocks 39 and are bridged by a slide member 42 that receives bars 41 in openings 43. Thumbscrews 44 are provided by the slide member 42 for anchoring that member in any position of vertical adjustment along bars 41. Similarly, the connecting blocks 39 are equipped with thumbscrews 45 so that such blocks may be fixed in desired positions along the horizontal stretches 35b of L-shaped bars 35.

An occipital contact plate 46 is carried at the forward (anterior) end of an adjustment rod 47, the rod extending through slide member 42 and being movable into different positions of horizontal adjustment. Thumbscrew 48 is carried by the slide member for anchoring rod 47 and plate 46 in position. As shown in FIG. 3, the face of plate 46 may be provided with a pad or cushion 49.

Means are also connected to the body plate 16 for rigidly supporting stereotaxic headring 11 in any of a variety of selected positions. A second pair of L-shaped support members or bars 50 are adjustably connected to mounting blocks or plates 34 as depicted clearly in FIG. 3. The downwardly extending portions 50a of such bars are received in elongated vertical openings 51 that parallel openings 36, and thumbscrews 52 are provided for anchoring the bars in place. A horizontal slide member 53 receives the horizontal portions 50b of the bars 50 and is equipped with a pair of upstanding parallel rods 54 for supporting ring clamps 55. The ring clamps are vertically slidable along bars 54 and are recessed at 56 to receive outer peripheral portions of the stereotaxic headring 11 (FIG. 1). Screws 57 may then be tightened to secure the clamps to the ring, and thumbscrews 58 may be tightened to secure the clamps to rods or posts 54. Similarly, thumbscrews 59, provided by slide member 53, may be tightened to fix that slide member in relation to support bars 50.

At the rear of the assembly, a slotted horizontal clamping plate 60 is carried by upstanding bars or rods 41, the plate being slotted or grooved at 61 to receive suitable connectors 62 provided by the headring for securing the headring to the plate. Thus, clamping or mounting plate 60, along with front (anterior) clamps 55, function to immobilize stereotaxic headring 11 in any selected position of adjustment with respect to brace 12.

Figure 5:
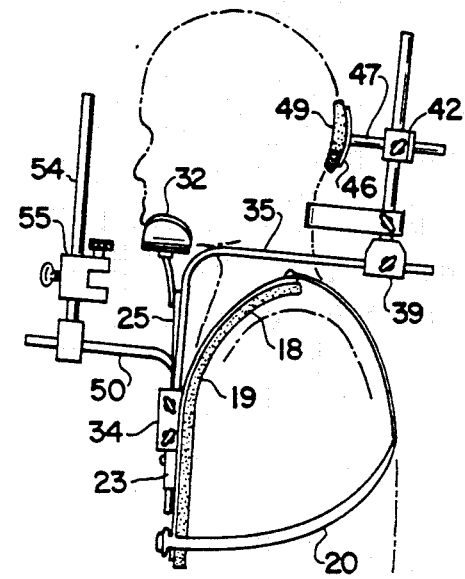
FIG. 5 is a side elevational view showing an early step of the method in which the bracing means is adjusted to fix a patient's head against movement in relation to his shoulders and upper torso, prior to the step (shown in FIG. 2) of securing the headring to the bracing system.

In use, the brace 12 is first fitted upon the patient as indicated in FIG. 5, with straps 20 adjusted to hold the body plate 16 firmly against the wearer's chest and shoulders. Chin support bar 25 is adjusted to position the chin plate 32 beneath the patient's chin, and support bars 35 are adjusted, along with connecting blocks 39, slide member 42, and support rod 47, to position head support plate 46 in firm contact with the occipital area of the patient's head. When the various thumbscrews are tightened, the head becomes effectively fixed against movement relative to the shoulders and upper torso.

Figure 2:
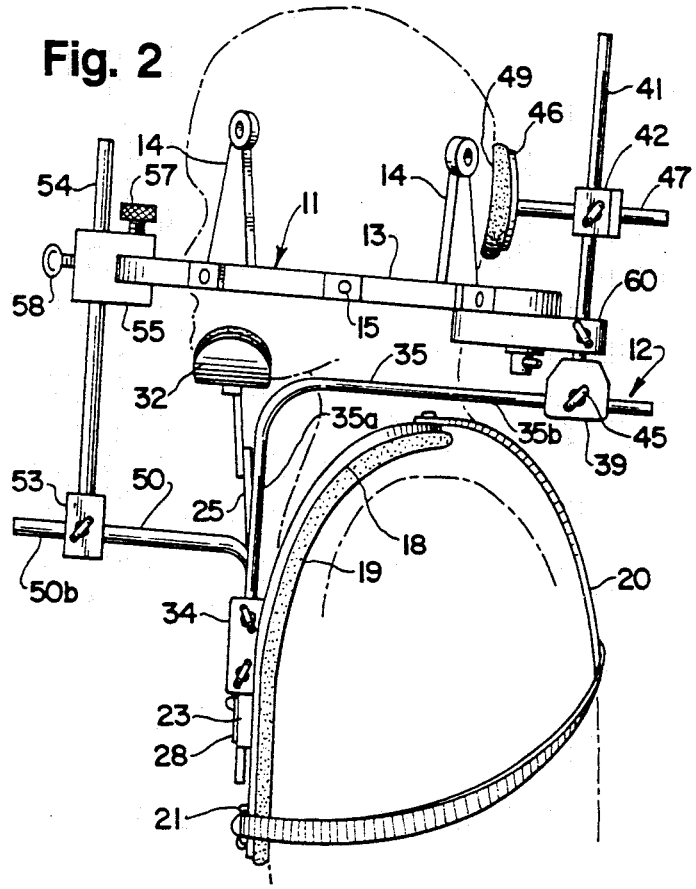
FIG. 2 is a side elevational view showing the headring and bracing means with the latter being fitted on a patient to immobilize the patient's head, and with the headring secured to the bracing means in a selected position of adjustment.

The head ring 11 is then fitted into place by coupling it to rear support plate 60 and front clamps 55, as shown in FIG. 2. It will be understood, however, that the headring may assume any of a variety of positions depending on the medical procedure and target location. For example, the ring may be angled for posterior fossa or extreme lateral temporal approaches. Also, the ring may be rotated for fine adjustment in the positioning of the fixation screws so as to minimize metal pin artifact in the CT plane of the target and allow for the identification of more comfortable entry sites of the screws into the skin and bone. Since the bracing of the patient's head and the mounting of the headframe occur in sequence, with the latter taking place only when the former has been achieved, the structure of this invention not only facilitates precise positioning of the headframe but also permits such steps be performed by a single person.

Figure 6:
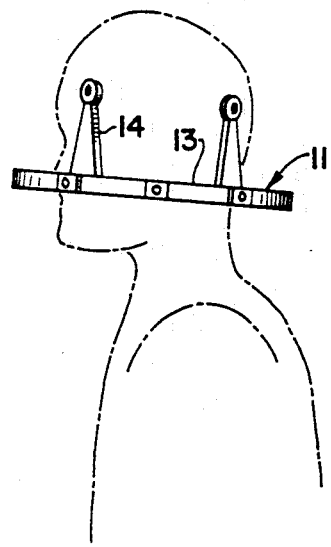
FIG. 6 is an elevational view similar to FIG. 5 but showing the headring after it has been secured to a patient's skull and the bracing system has been removed.

Once optimal positioning of the headring is achieved, local anesthetic is applied at the screw entry points and screws of nylon or polytetrafluoroethylene are inserted through openings 14a and affixed to the calvarium in the usual manner. The bracing system is then removed, leaving the stereotaxic headring in place as depicted in FIG. 6.

As previously indicated, the bracing system is formed of rigid components, the body plate 16 being composed of metal or rigid plastic and the support bars, such as 25, 35, 41, 47, 50, and 54, being formed of metal such as, for example, stainless steel. Other parts, such as mounting blocks 34, connecting blocks 39, clamping plate 60, clamps 55, and slide members 42 and 53, are advantageously formed of a rigid, durable, polymeric material such as polytetrafluoroethylene.

While in the foregoing, I have disclosed an embodiment of the invention in considerable detail for purposes of illustration, it will be understood by those skilled in the art that many of these details may be varied without departing from the spirit and scope of the invention.

I claim:

1. In combination, a headring for stereotaxic neurosurgery and bracing means for applying said headring; said headring being dimensioned to extend around a patient's head and having anchoring means for rigidly securing said headring to the patient's skull; said bracing means consisting essentially of a rigid chest plate having a pair of rigid shoulder rests for supporting said bracing means on a patient's shoulders and strap means for immobilizing said chest plate relative to the patient's shoulders and upper torso; a plurality of support members for said headring exclusively and adjustably mounted upon said chest plate; and a plurality of clamping members adjustably mounted upon said support members and circumferentially and releasably engagable with said headring; chin support means adjustably secured to said chest plate for holding the chin of the patient in fixed position; and occipital support means adjustably supported by said chest plate for contacting the occiput to immobilize the head in relation to said chest plate.

2. The combination of claim 1 in which said chest plate is Y-shaped in configuration and includes a central portion from which said rigid shoulder rests extend upwardly and posteriorly; said straps being connected to posterior ends of said shoulder rests and being extendible over a patient's back and about the waist for connection to said central portion of said plate; and adjustable connecting means provided by said strap and said central portion for connecting the same together and for holding said plate firmly against a patient's chest.

3. The combination of claim 1 in which mounting means are provided on said chest plate for adjustably supporting two pairs of said support members; said two pairs of support members including rigid support bars each having horizontal and vertical portions; said vertical portions of said support bars being slidably received in openings in said mounting means; and screw means for securing said vertical portions to said mounting means in selected positions of adjustment.

4. The combination of claim 3 in which one of said two pairs of said rigid support bars have horizontal portions extending posteriorly over a patient's shoulders; connecting means joined to said posteriorly-extending horizontal portions and adjustably connecting said portions to a pair of upstanding bars positioned behind a patient's head; said occipital support means including an adjustable slide member carried by said upstanding bars and equipped with an adjustable head plate for engaging the occiput of a patient.

5. The combination of claim 4 in which said clamping members include a clamping plate slidably mounted upon said pair of upstanding bars for supporting and securing said headring in an area behind a patient's head.

6. The combination of claim 3 in which said clamping members include a pair of clamps adjustably supported by a pair of generally vertical bars; and a slide member secured to the lower ends of said vertical bars and adjustably supporting the same on horizontal and forwardly-extending portions of one of said two pairs of support bars.

7. A brace for bracing a patient's head and for supporting a stereotaxic headring for neurosurgery, comprising a rigid chest plate having a pair of rigid shoulder rests for supporting said brace on a patient's shoulders and strap means for immobilizing said plate relative to a patient's shoulders and upper torso; a plurality of rigid headring support members exclusively and adjustably mounted upon said chest plate; a plurality of clamping members adjustably mounted upon said support members for circumferentially and releasably engaging a stereotaxic headring; chin-support means adjustably secured to said chest plate for holding the chin of a patient in fixed position; occipital support means adjustably supported by said chest plate for contacting the occiput to immobilize the head in relation to said chest plate; and mounting means provided on said chest plate for adjustably supporting two pairs of said support members; said two pairs of support members including rigid support bars each having horizontal and vertical portions; said vertical portions of said support bars being slidably received in openings in said mounting means; and screw means for securing said vertical portions to said mounting means in selected positions of adjustment; one of said two pairs of said rigid support bars having horizontal portions extending posteriorly over a patient's shoulders; connecting means joined to said posteriorly-extending horizontal portions and adjustably connecting said portions to a pair of upstanding bars positioned behind a patient's head; said occipital support means including an adjustable slide member carried by said upstanding bars and equipped with an adjustable head plate for engaging the occiput of a patient.

8. The brace of claim 7 in which said clamping members include a clamping plate slidably mounted upon said pair of said upstanding bars for supporting and securing a portion of a headring extending behind a patient's head.

9. A brace for bracing a patient's head and for supporting a stereotaxic headring for neurosurgery, comprising a rigid chest plate having a pair of rigid shoulder rests for supporting said brace on a patient's shoulders and strap means for immobilizing said plate relative to a patient's shoulders and upper torso; a plurality of rigid headring support members exclusively and adjustably mounted upon said chest plate; a plurality of clamping members adjustably mounted upon said support members for circumferentially and releasably engaging a stereotaxic headring; chin-support means adjustably secured to said chest plate for holding the chin of a patient in fixed position; occipital support means adjustably supported by said chest plate for contacting the occiput to immobilize the head in relation to said chest plate; and mounting means provided on said chest plate for adjustably supporting two pairs of said support members; said two pairs of support members including rigid support bars each having horizontal and vertical portions; said vertical portions of said support bars being slidably received in openings in said mounting means; and screw means for securing said vertical portions to said mounting means in selected positions of adjustment; said clamping members including a pair of clamps adjustably supported by a pair of generally vertical bars; and a slide member secured to the lower ends of said vertical bars and adjustably supporting the same on horizontal and forwardly-extending portions of one of said two pairs of said support bars.

* * * * *